US011559333B2

(12) United States Patent
Capote et al.

(10) Patent No.: US 11,559,333 B2
(45) Date of Patent: Jan. 24, 2023

(54) BONE ANCHOR

(71) Applicant: Zimmer Biomet Spine, Inc., Westminster, CO (US)

(72) Inventors: Allison Christine Capote, Boulder, CO (US); Randall G. Mast, Denver, CO (US); Jared Parker, Denver, CO (US); Thomas Serra, Arvada, CO (US); Caleb Lee Stoll, Broomfield, CO (US)

(73) Assignee: Zimmer Biomet Spine, Inc., Westminster, CO (US)

( * ) Notice: Subject to any disclaimer, the term of this patent is extended or adjusted under 35 U.S.C. 154(b) by 38 days.

(21) Appl. No.: 16/694,098

(22) Filed: Nov. 25, 2019

(65) Prior Publication Data

US 2020/0229847 A1 Jul. 23, 2020

Related U.S. Application Data

(60) Provisional application No. 62/794,838, filed on Jan. 21, 2019.

(51) Int. Cl.
*A61B 17/70* (2006.01)
*A61B 17/86* (2006.01)

(52) U.S. Cl.
CPC ...... *A61B 17/7032* (2013.01); *A61B 17/7007* (2013.01); *A61B 17/7037* (2013.01); *A61B 17/8625* (2013.01); *A61B 2017/8655* (2013.01)

(58) Field of Classification Search
CPC ............. A61B 17/7032–17/7037; A61B 17/70
See application file for complete search history.

(56) References Cited

U.S. PATENT DOCUMENTS

| | | | |
|---|---|---|---|
| 7,875,065 B2 | 1/2011 | Jackson | |
| 9,168,069 B2 | 10/2015 | Jackson et al. | |
| 9,603,630 B2 | 3/2017 | Farris | |
| 9,763,700 B1 | 9/2017 | Gregory | |
| 9,820,782 B2 | 11/2017 | Daniels | |
| 9,924,971 B2 | 3/2018 | Biedermann et al. | |
| 10,034,691 B1 | 7/2018 | Lish | |
| 2004/0236330 A1 | 11/2004 | Purcell et al. | |
| 2005/0283157 A1 | 12/2005 | Coates et al. | |
| 2007/0088357 A1 | 4/2007 | Johnson et al. | |
| 2008/0154315 A1* | 6/2008 | Jackson | A61B 17/7035 606/309 |
| 2008/0161859 A1 | 7/2008 | Nilsson | |
| 2010/0137918 A1* | 6/2010 | Wilcox | A61B 17/7037 606/301 |
| 2011/0178559 A1 | 7/2011 | Barry | |
| 2011/0202094 A1* | 8/2011 | Pereira | A61B 17/7037 606/305 |

(Continued)

FOREIGN PATENT DOCUMENTS

EP 2964115 A1 1/2016

OTHER PUBLICATIONS

U.S. Appl. No. 16/550,637, filed Aug. 26, 2019, Bone Anchor.

(Continued)

*Primary Examiner* — Eduardo C Robert
*Assistant Examiner* — Michelle C Eckman
(74) *Attorney, Agent, or Firm* — Sheridan Ross P.C.

(57) ABSTRACT

An anchor assembly can be couplable to a bone and can include an anchor and a housing. The anchor can include a shank securable to bone and a head coupled to a proximal portion of the shank.

18 Claims, 6 Drawing Sheets

(56) References Cited

U.S. PATENT DOCUMENTS

| | | | |
|---|---|---|---|
| 2012/0016425 A1 | 1/2012 | Shaffrey et al. | |
| 2012/0059426 A1 | 3/2012 | Jackson et al. | |
| 2014/0257411 A1* | 9/2014 | Rezach | A61B 17/7037 606/305 |
| 2015/0282844 A1 | 10/2015 | Vedula et al. | |
| 2015/0297266 A1* | 10/2015 | Kirschman | A61B 17/7032 606/266 |
| 2016/0262817 A1* | 9/2016 | Rezach | A61B 17/8605 |
| 2016/0331412 A1* | 11/2016 | Biedermann | A61B 17/7037 |
| 2017/0135732 A1 | 5/2017 | Jackson et al. | |
| 2017/0245898 A1* | 8/2017 | May | A61B 17/7032 |
| 2017/0333085 A1 | 11/2017 | Jackson et al. | |
| 2020/0069344 A1 | 3/2020 | Capote | |

OTHER PUBLICATIONS

"U.S. Appl. No. 16/550,637, Final Office Action dated Apr. 7, 2021", 11 pgs.

"U.S. Appl. No. 16/550,637, Non Final Office Action dated Jan. 13, 2021", 24 pgs.

"U.S. Appl. No. 16/550,637, Advisory Action dated Jun. 2, 2021", 3 pgs.

"U.S. Appl. No. 16/550,637, Response filed Mar. 8, 2021 to Non Final Office Action dated Jan. 13, 2021", 17 pgs.

"U.S. Appl. No. 16/550,637, Response filed May 20, 2021 to Final Office Action dated Apr. 7, 2021", 13 pgs.

"European Application Serial No. 19194424.8, Extended European Search Report dated Jan. 23, 2020", 10 pgs.

"European Application Serial No. 19194424.8, Response filed Sep. 4, 2020 to Extended European Search Report dated Jan. 23, 2020", 18 pgs.

"European Application Serial No. 20152733,0, Extended European Search Report dated Jun. 19, 2020", 9 pgs.

"European Application Serial No. 20152733.0, Response filed Jan. 22, 2021 to Extended European Search Report dated Jun. 19, 2020", 16 pgs.

"U.S. Appl. No. 16/550,637, Non Final Office Action dated Jul. 7, 2021", 10 pages.

"U.S. Appl. No. 16/550,637, Examiner Interview Summary dated Aug. 31, 2021", 2 pages.

"U.S. Appl. No. 16/550,637, Response filed Sep. 20, 2021 to Non Final Office Action dated Jul. 7, 2021", 12 pages.

* cited by examiner

BONE ANCHOR

CLAIM OF PRIORITY

This application claims the benefit of U.S. Provisional Patent Application Ser. No. 62/794,838, filed on Jan. 21, 2019, the benefit of priority of which is claimed hereby, and which is incorporated by reference herein in its entirety.

BACKGROUND

This document pertains generally, but not by way of limitation, to systems and methods for fixation of bones during orthopedic procedures. More particularly, this disclosure relates to, but not by way of limitation, vertebral bone anchors. Orthopedic devices such as rods, plates, tethers, staples, and other devices can be used in various spinal procedures to correct abnormalities (e.g., scoliosis) or to address injuries (e.g., vertebral fracture). In some spinal procedures, anchors and rods can be secured along a vertebral column to vertebrae to stabilize a region of the spine. In these procedures, pedicle screws (or vertebral anchors) can be secured to individual vertebra and tied together with a connecting rod.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

This application file contains at least one drawing executed in color. Copies of this patent or patent application publication with color drawing(s) will be provided by the Office upon request and payment of the necessary fee.

DETAILED DESCRIPTION

Bone anchors can be used together with connecting members (such as rigid and semi-rigid rods) to straighten a region of a human spine to address an abnormality (e.g., scoliosis), to stabilize a spine following an injury (e.g., fractured vertebrae), or to address degeneration of the spine caused by disease. In one example procedure, anchors are driven into vertebrae and are manipulated from outside of the cavities. The housing of the anchor can be positioned with respect to the shank of the anchor and the housings can be individually and collectively positioned along the spinal column to receive a connecting rod. The connecting rod can extend through two or more housings and can be secured to each housing by a closure top or set screw.

In some procedures, disruption of muscle around the vertebral column may be reduced by using a technique that secures vertebral anchors along a cortical trajectory. That is, the trajectory along which the shank of the anchor extends into the vertebra to which it is secured can be through primarily cortical bone. This is opposed to a standard trajectory where the shank can extend into the vertebral body. In addition to helping to limit muscle disruption, this technique may enable use of smaller diameter and length anchors while maintaining good fixation. However, to allow for proper support of the connecting member to the housing, the cortical trajectory can require relatively larger angulation of the shank with respect to the housing of the anchor in the medial to lateral and/or caudal to cranial directions. Further, because these procedures are performed with relative little work space (within a retracted opening), it is desirable to achieve relatively large angulation at multiple positions of the shank relative to the housing while still retaining the shank within the housing.

In some examples, this disclosure addresses these problems by including a turret couplable to a distal portion of a housing of an anchor. More specifically, to provide the angulation required for use of a cortical trajectory, this disclosure proposes to use a turret including a relatively larger bore in the turret where the turret is configured to rotate with respect to the housing, in one example, to allow for a relatively high degree of angulation of the anchor relative to the housing to allow the cortical trajectory to be used while still allowing the housings to be aligned to accept a connecting rod.

In one example, this disclosure addresses these problems by including a multi-piece anchor. More specifically, to provide the angulation required for use of a cortical trajectory, this disclosure proposes to use an anchor including a separate head and shank that are couplable together.

This discussion is intended to provide an overview of subject matter of the present patent application. It is not intended to provide an exclusive or exhaustive explanation of the invention. The discussion below is included to provide further information about the present patent application.

Figure 1A:
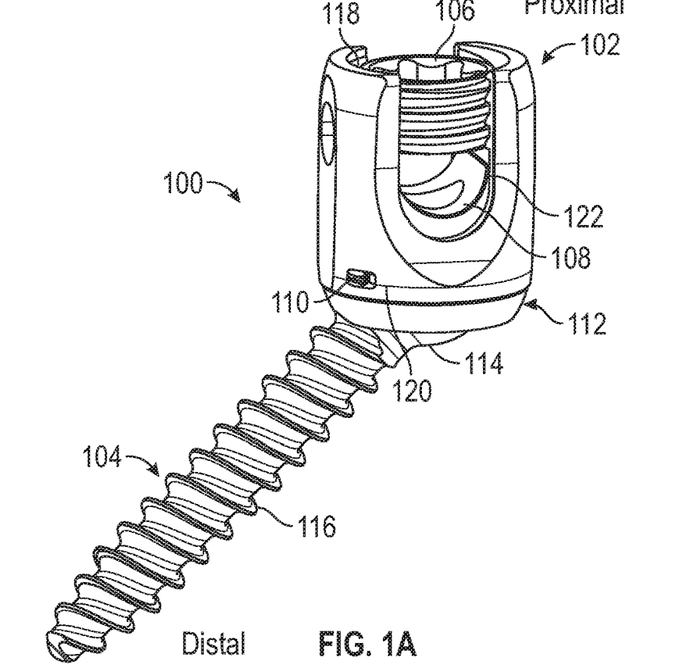
FIG. 1A illustrates an isometric view of an anchor assembly, in accordance with at least one example of this disclosure.
Figure 1B:
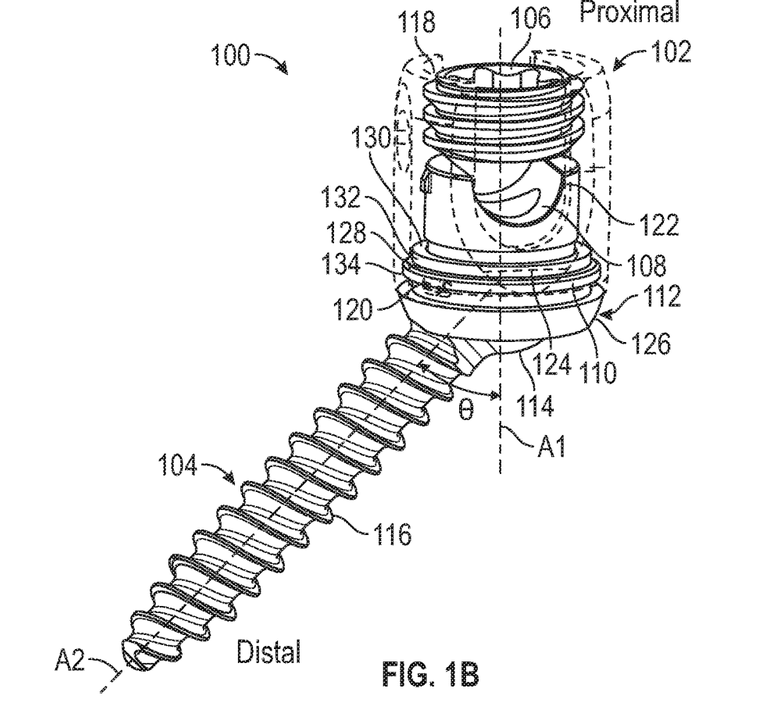
FIG. 1B illustrates an isometric view of an anchor assembly with a portion of the anchor assembly in phantom, in accordance with at least one example of this disclosure.

FIG. 1A illustrates an isometric view of an anchor assembly 100, in accordance with at least one example of this disclosure. FIG. 1B illustrates an isometric view of the anchor assembly 100 with a housing 104 of the anchor assembly 100 shown in phantom, in accordance with at least one example of this disclosure. FIGS. 1A and 1B are discussed below concurrently.

The anchor assembly 100 can include a housing 102, an anchor 104, a set screw 106, a saddle 108, a locking element 110, and a turret 112. The anchor 104 can include a head 114 and a shank 116. The housing 102 can include a central bore 118, a lock opening 120, and channels 122. The turret 112 can include a proximal portion 124, and a distal portion 126. The distal portion can include a lock channel 128 (or turret channel), and a saddle bore 130. Also shown in FIG. 1 are axes A1 and A2, angle θ, and orientation indicators Proximal and Distal.

The anchor assembly 100 can be a fastener configured to secure to a work piece, such as a bone, plate, prosthesis, or other device used in a surgery or operation. In other examples, the anchor assembly 100 can be configured to engage wood, plastics, metals, and the like, for applications outside of surgical procedures. The anchor assembly 100 can be comprised of one or more of plastics, metals, composites, combinations thereof, or the like. The anchor assembly 100 can be comprised of biocompatible materials such as such as one or more of stainless steels, cobalt-chromium, titanium variations, polyether ether ketone (PEEK), or combinations thereof.

The housing 102 of the anchor 100 can be a rigid member coupled to the turret 112 at a distal portion of the housing 102. The central bore 118 can be a bore extending through the housing 102 along the axis A1, where the axis A1 can be a central axis for the housing 102. The channels 122 can be generally U-shaped channels in the housing 102 configured to receive a rod or connecting member therethrough.

The head 114 can be located at a proximal portion of the anchor 104 and can be connected to the shank 116. The head 114 can have a diameter larger than that of the shank 116 such that the shank 116 can extend through the housing 102 and so that the head 114 can be limited from passing through a distal opening of the housing 102 (or through the turret 112). The shank 116 can extend distally away from the head 114 and can include a threaded portion for engaging bone. In some examples, the shank 116 (and anchor 104) can deviate from the axis A1 at various angles, such as angle θ when the shank 116 is along axis A2.

The set screw 106 can be a screw or fastener securable to a proximal portion of the housing 102 to retain a connecting member within the housing 102 between the set screw 106 and the saddle 108. The saddle 108 be a supporting member that can be configured to be supported by the turret 112 in the saddle bore 130. The saddle 108 can also be configured to support the connecting member.

The lock 110 can be a semi-rigid member insertable into the lock opening 120 of the housing 102, as discussed below. The lock 110 can be a flexible member and can have a geometric shape of a bar or cylinder, such as a cylindrical wire. The lock 110 can be comprised of one or more flexible materials such as plastics, metals, or the like, and the lock 110 can be made of spring steel in some examples. The lock 110 can be comprised of a material having a shape memory, such as nitinol.

The turret 112 can include the proximal portion 124 and the distal portion 126, where the proximal portion 124 has a relatively smaller diameter for insertion into the central bore 118. In some examples, the central bore 118 can include an undercut 132 to receive the proximal portion 124 therein. The distal portion 126 can have a relatively larger diameter to limit translation of the turret 112 into the housing 102.

The proximal portion 124 can include the turret channel 128, which can be a circumferential channel of the proximal portion 124. The turret channel 128 can extend around a circumference of the proximal portion 124 in some examples, and can extend substantially around the proximal portion 124 in other examples. In operation, the turret channel 128 can be sized and shaped to receive the lock 110 therein. And, the turret channel 128 can align with the lock opening 120 of the housing when the turret 112 is inserted into the housing 102.

In assembly of some examples, the proximal portion 124 of the turret 112 can be inserted into a distal portion of the housing 102 until the proximal portion 124 and/or the distal portion 126 contacts the housing. The lock 110 can then be inserted into the lock opening 120 and into the turret channel 128 of the proximal portion and a lock channel 134 of the housing 102 (when the channel 128 and the lock channel 134 are aligned). The lock channel 134 of the housing 102 can extend substantially around an inner circumference of the housing 102 and can be interrupted by the lock opening 120.

The lock 110 can flex or bend to contour to a shape of the channels 128 and 134 as the lock 110 is inserted into the channels 128 and 134 and around (a substantial portion of) the circumference of the proximal portion 124. The lock 110 can substantially fill the gap created by the lock channels 128 and 134 and can thereby prevent relative translation of the turret 112 with respect to the housing 102. In some examples, the lock 110 can be secured to the housing 102 following complete insertion into the lock opening 120, such as by welding or fastening.

Once the turret 112 is secured to the housing 102, the shank 116 of the anchor 104 can be inserted proximally-to-distally through the central bore 118 of the housing 102 and the turret 112, such that the shank 114 extends distally out of the turret 112. In some examples, the shank 114 can then be secured to a bone of a patient. The housing 102 can then be positioned relative to the anchor 104 as the head 114 of the anchor 102 can articulate within the turret 112. For example, the anchor 104 can be positioned at the angle θ when the shank is positioned along the axis A2 with respect to the central axis A1 of the housing 102.

Then, the saddle 108 can be inserted into the central bore 118 such that the distal portion of the piston 108 rests within the saddle bore 130 of the turret 112 to limit relative movement thereof. The saddle 108 also takes up space within the turret 112 to help prevent the turret 112 from compressing inward (due to forces of the anchor 104 and connecting member). The saddle 108 can receive the connecting member therein, which can be secured within the housing 102 by the set screw 106. In some examples, the set screw 106 applies a downward force resulting in a friction fit between the turret 112 and the housing 102, which can help prevent rotation of the turret 112 relative to the housing 102.

A distal opening of the distal portion 126 of the turret 112 can be configured to allow the anchor 104 to be oriented at various angles with respect to axis A1 and therefore relative to the housing 102 and to the bone. In some examples, the turret 112 can be rotatable with respect to the housing 102 to allow for the anchor 104 to be positioned at various and relatively extreme angles (such as 30 degrees, 35 degrees, 40 degrees, or the like) with respect to axis A1 to allow for the anchor 104 to be secured to a vertebra using a cortical bone technique. Though this disclosure references use of anchor assembly 100 using a cortical trajectory technique, the anchor assembly 100 can be used in various other vertebral anchoring techniques where the benefits of the anchor assembly 100 (such as the anchor 104 can be oriented at various angles with respect to the housing 102) can be useful.

In some examples, the lock 110 can be other components, such as a cut ring (of one or more pieces), a plurality of ball bearings, one or more pins, or one or more snap rings. In some examples, the lock 110 can have a cylindrical profile, but can have other profile shapes in other examples, such as a square prism.

Figure 2A:
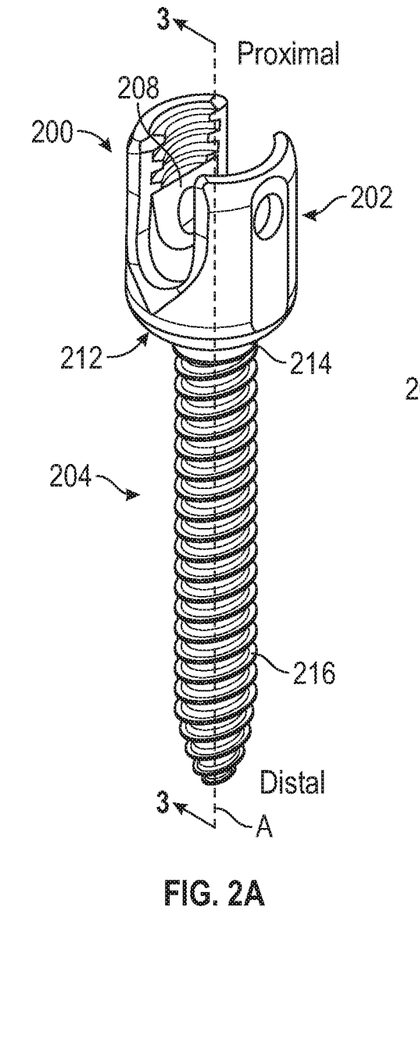
FIG. 2A illustrates an isometric view of an anchor assembly, in accordance with at least one example of this disclosure.
Figure 2B:
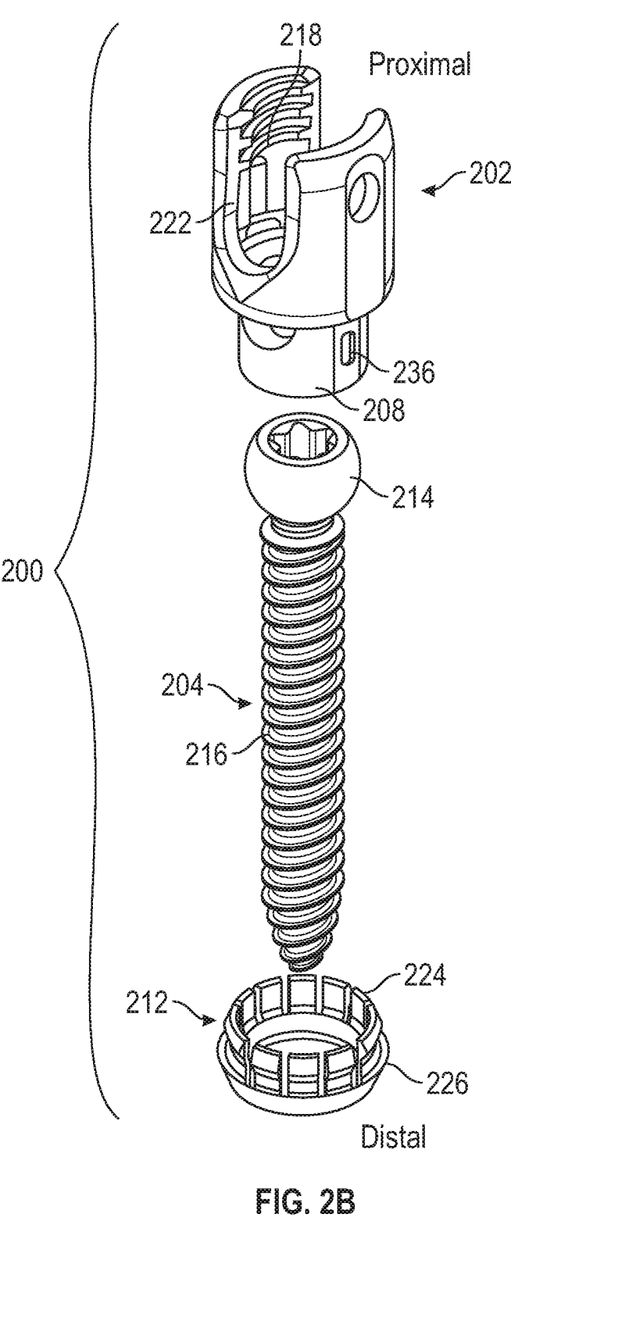
FIG. 2B illustrates an exploded isometric view of an anchor assembly, in accordance with at least one example of this disclosure.

FIG. 2A illustrates an isometric view of an anchor assembly 200, in accordance with at least one example of this disclosure. FIG. 2B illustrates an exploded isometric view of the anchor assembly 200, in accordance with at least one example of this disclosure. The anchor assembly 200 can include a turret securable to a housing using cantilevered fingers or barbs. Any of the previously (or later) discussed anchor assemblies can be modified to include such a turret.

The anchor assembly 200 can include a housing 202, an anchor 204, a saddle 208, and a turret 212. The anchor 204 can include a head 214 and a shank 216. The housing 202 can include a central bore 218, and channels 222. The turret 212 can include a proximal portion 224, and a distal portion 226. The saddle 208 can include a saddle boss 236 and can receive a connecting member 235. Also shown in FIGS. 2A and 2B are axis A, section indicators 3-3, and orientation indicators Proximal and Distal.

The components of the anchor assembly 200 can be similar to the anchor assembly 100 discussed above, except that the saddle 208 can be configured to rest on the head 214 of the anchor 204 and FIG. 2B shows the saddle boss 236, which can be a boss of the saddle 208 extending radially outward therefrom to engage the housing, which can help reduce rotation of the saddle 208 within the housing 202, as discussed below.

The anchor assembly 200 can also differ in that the proximal portion 224 of the turret 212 can include proximally extending fingers configured to secure the turret 212 to the housing 202. In assembly of some examples, the anchor assembly 200 can be a bottom-loading assembly, where the saddle 208 can be inserted distally-to-proximally into the housing 202 until the saddle engages the housing 202. The anchor head 214 can then be inserted distally-to-proximally into the housing 202 until the head 214 engages the saddle. The turret 212 can then be passed over the shank 216 and can be forced in a proximal direction into the housing 202 until the fingers of the proximal portion 224 deflect radially inward and insert into a bore of the housing.

Figure 3:
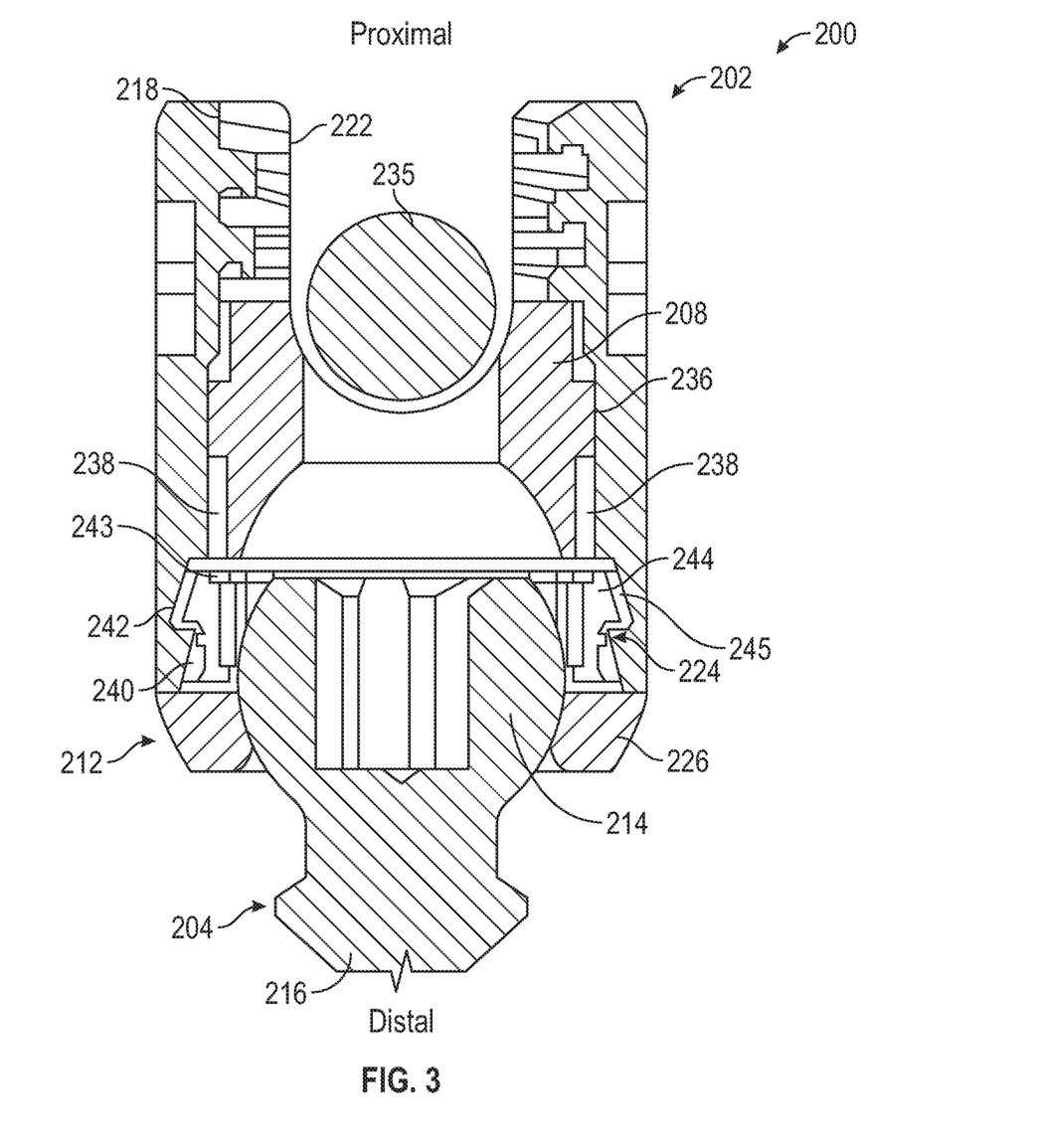
FIG. 3 illustrates a cross-section view of an anchor assembly across section 3-3 of FIG. 2A, in accordance with at least one example of this disclosure.

FIG. 3 illustrates a cross-section view of the anchor assembly 200 across section 3-3 of FIG. 3A, in accordance with at least one example of this disclosure. The anchor assembly 200 of FIG. 3 can be consistent with FIGS. 2A and 2B above, while showing additional details of the anchor assembly 200. For example, FIG. 3 shows how the saddle boss 236 can reside in a boss slot 238 of the housing 202. This engagement can prevent the saddle 208 from rotating with respect to the housing 202 and can limit proximal translation of the saddle 208 with respect to the housing 202.

FIG. 3 also shows that the saddle 208 can be configured to receive the connecting member 235 therein to retain the connecting member 235 within the housing 202. A set screw or closure top (such as set screw 106 of FIGS. 1A and 1B) can be threaded into the housing 202 to secure the connecting member 235 within the housing 202.

FIG. 3 also shows that the housing 202 can include a turret bore 240 including an undercut 242. The turret bore 240 can be positioned at a distal opening of the housing 202 and can extend proximally into the housing 202 therefrom, where the turret bore 240 can taper radially inward from the distal opening of the housing 202. The undercut 242 can extend radially outward from the turret bore 240 and can be sized to receive fingers 244 of the proximal portion 224 of the turret 212. The undercut 242 can taper radially inward from the turret bore 240 before terminating within the housing 202. The fingers 244 can include barbs 245 extending radially outward and tapering distally. The barbs, prongs, or tines 245 can be configured to engage a proximal surface of the undercut 242 to limit axially distal translation of the turret 212 with respect to the housing 202.

The fingers 244 can also form a saddle bore 243 on a radially inner surface of the fingers 244. The saddle bore 243 can be sized and shaped to receive the saddle 208 within the saddle bore 243 on the back or radially inner surface of the fingers 244. The saddle bore 243 can be positioned such that the saddle 208 can contact the radially inner portion of the fingers 244 to bias the fingers 244 radially outwards to limit the fingers 244 from deflecting inward due to forces of the anchor 204 and the connecting member 235. This can help reduce failure of the anchor assembly 200 due to over-torqueing of the anchor or due to high forces during a procedure, such as de-rotation, or from failure caused by post-operative patient activities.

FIG. 3 also shows how the fingers 224 can be cantilevered proximally from the distal portion 226 and can have a barb shaped portion biased radially outward and deflectable radially inward. In some examples, the fingers 244 can deflect inward to allow insertion of the proximal portion 224 into the turret bore 240 and the fingers 244 can be biased radially outward to snap into the undercut 242 when the fingers 244 are in alignment with the undercut 242. In such examples, the barb shaped portion can be configured to engage the undercut 242 to retain the turret 212 within the turret bore 240.

Figure 4A:
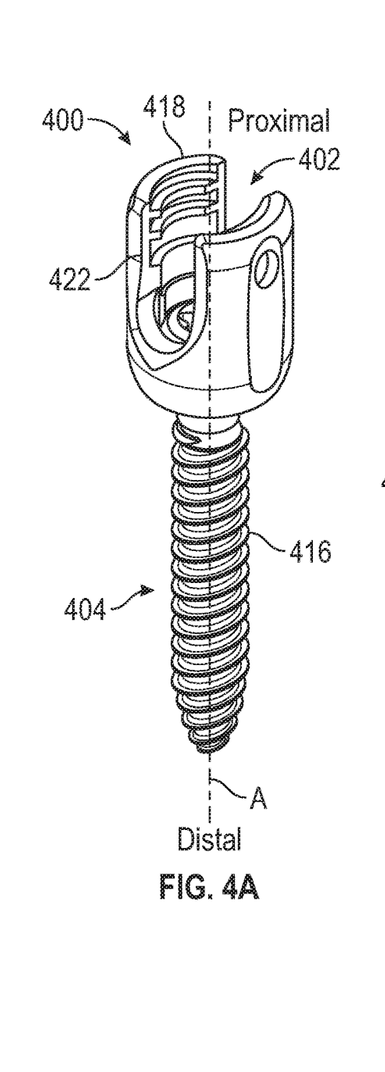
FIG. 4A illustrates an isometric view of an anchor assembly, in accordance with at least one example of this disclosure.
Figure 4B:
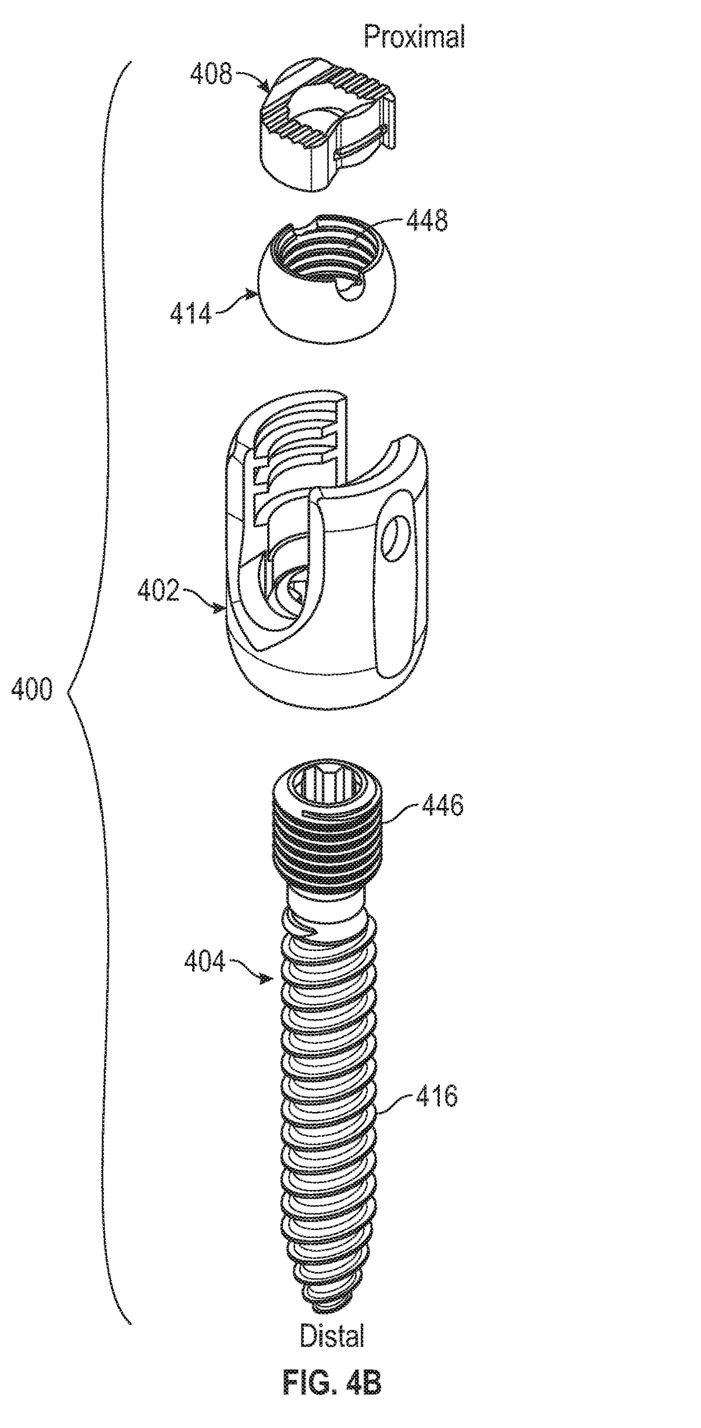
FIG. 4B illustrates an exploded isometric view of an anchor assembly, in accordance with at least one example of this disclosure.

FIG. 4A illustrates an isometric view of an anchor assembly 400, in accordance with at least one example of this disclosure. FIG. 4B illustrates an exploded isometric view of the anchor assembly 400, in accordance with at least one example of this disclosure. The anchor assembly 400 can include a multi-piece anchor securable to a housing. Any of the previously (or later) discussed anchor assemblies can be modified to include such an anchor The anchor assembly 400 can include a housing 402, an anchor 404, a saddle 408, and a donut 414 (or head). The anchor 404 can include a proximal threaded portion 446 and a shank 416. The housing 402 can include a central bore 418, and channels 422. The donut 414 can include a threaded portion 448. Also shown in FIGS. 4A and 4B are axis A and orientation indicators Proximal and Distal.

The components of the anchor assembly 400 can be similar to the anchor assemblies 100 and 200 discussed above, except that the anchor 404 can include the proximal threaded portion 446, which can be threadably secured to the threaded portion 448 of the donut 414. The donut 414 can be configured to operate as a head of the anchor 404 within the housing 402. The ability to thread the threaded portion 448 of the anchor 404 into the donut 414 provides for a bottom-loading design, which further allows a dimeter of the shank 416 to be larger than an internal diameter of the housing 402. In other examples, the anchor assembly 400 can be a top-loading design when the diameter of the shank 416 is smaller than the housing diameter. In some examples, the shank 416 can have a dimeter smaller than a dimeter of the donut 414 and the saddle 408 such that the shank 416 can be passed through the housing 402, the donut 414, and the saddle 408, where the shank 416 can act as a fasten to hold all of these components (the housing 402, the donut 414, and the saddle 408) together. In such a top-loading design, the housing 402, the donut 414, and the saddle 408 may not be threaded and can include interlocking features, such as flats.

In assembly of some examples, the donut 414 can be inserted into the housing 402 while in a 90-degree rotated position (such that the bore is orthogonal to the axis A. Once the donut 414 is fully inserted into the housing 402, the donut 414 can be rotated into its place in a mating spherical cutout in of the housing 412, such that the bore of the donut 414 is coaxial with the axis A. The proximal portion 446 can then be secured to the donut 414. The assembly 400 therefore allows for the donut 414, which can act as a spherical head of the shank 416, to be relatively larger than if the anchor 404 included an integral head.

Figure 5A:
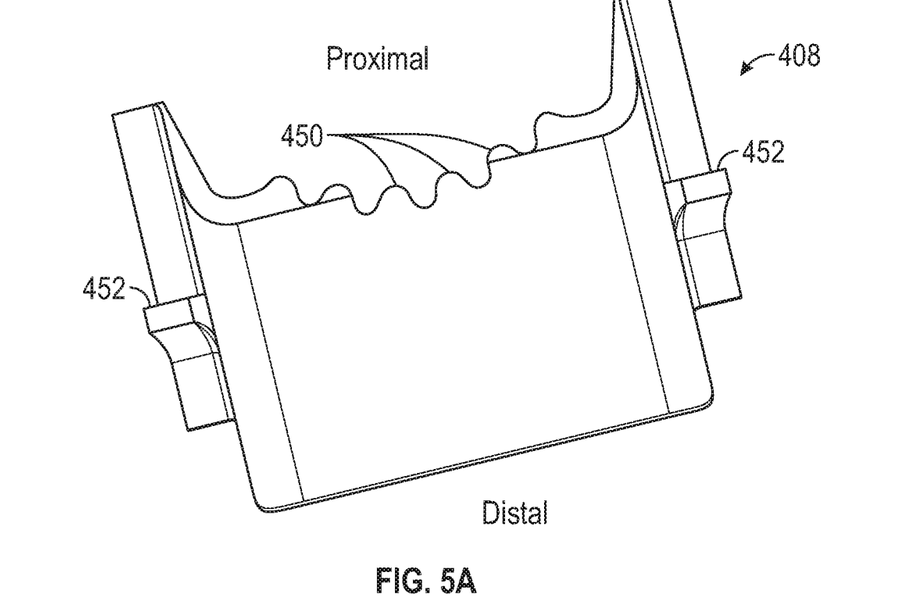
FIG. 5A illustrates an isometric view of a portion of an anchor assembly, in accordance with at least one example of this disclosure.
Figure 5B:
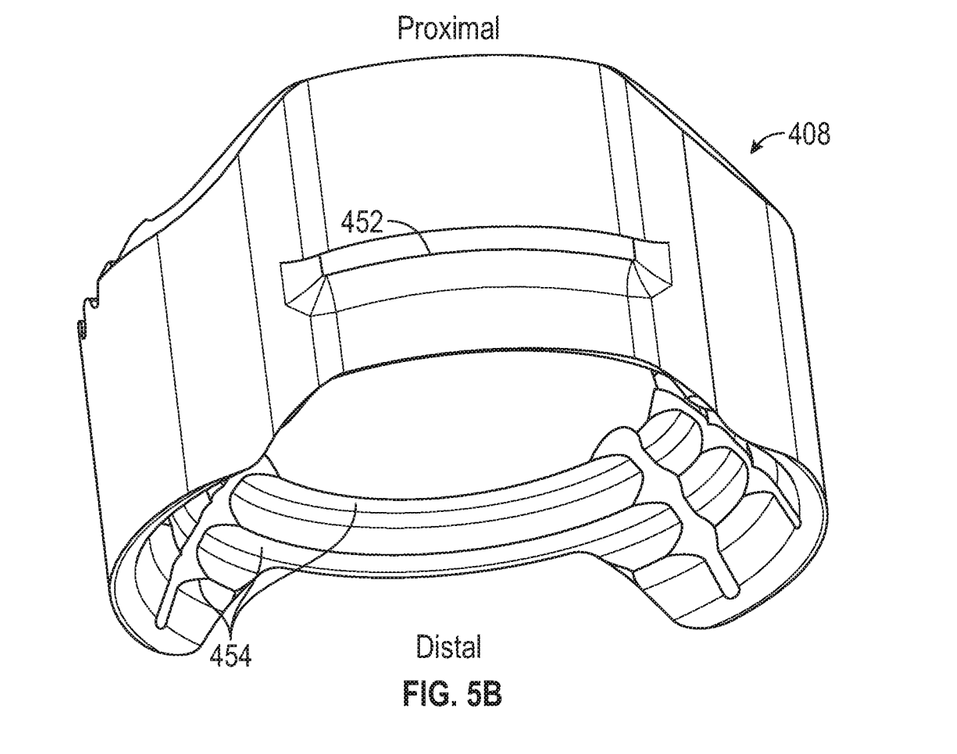
FIG. 5B illustrates an isometric view of a portion of an anchor assembly, in accordance with at least one example of this disclosure.

FIG. 5A illustrates an isometric view of the saddle 408 of the anchor assembly 400, in accordance with at least one example of this disclosure. FIG. 5B illustrates an isometric view of the saddle 408 of the anchor assembly 400, in accordance with at least one example of this disclosure. FIGS. 5A and 5B are discussed below concurrently. Shown in FIGS. 5A and 5B are orientation indicators Proximal and Distal.

FIG. 5A shows engagement teeth 450, which can be one or more teeth or ledges extending proximally from the saddle 408. The engagement teeth 450 can be configured to engage a connecting rod within the housing 402. The teeth 450 can be configured to contact a connecting rod to help prevent relative movement of the connecting rod within the housing 402 when the connecting rod is compressed between a set screw and the saddle 408.

FIG. 5A also shows ledges 452, which can extend radially outward from a radially outer surface of the saddle 408 and can be tapered distally to create a proximal-facing flat face for retaining the saddle 408 within the housing 402. The ledges 452 can snap into a bore of the housing 402 to help retain the saddle 408 axially.

FIG. 5A also shows teeth 454 (or ridges), which can be formed by concentric channels or ridges to create teeth extending radially inward and/or distally from an internal surface of the saddle 408 and toward a direction of a head of the anchor when the saddle 408 is engaged with the head. In some examples, the teeth 454 can be configured to engage the donut 414 to help limit relative movement between the donut 414 and the saddle 408 and therefore between the anchor 404 and the housing 402.

Figure 6:
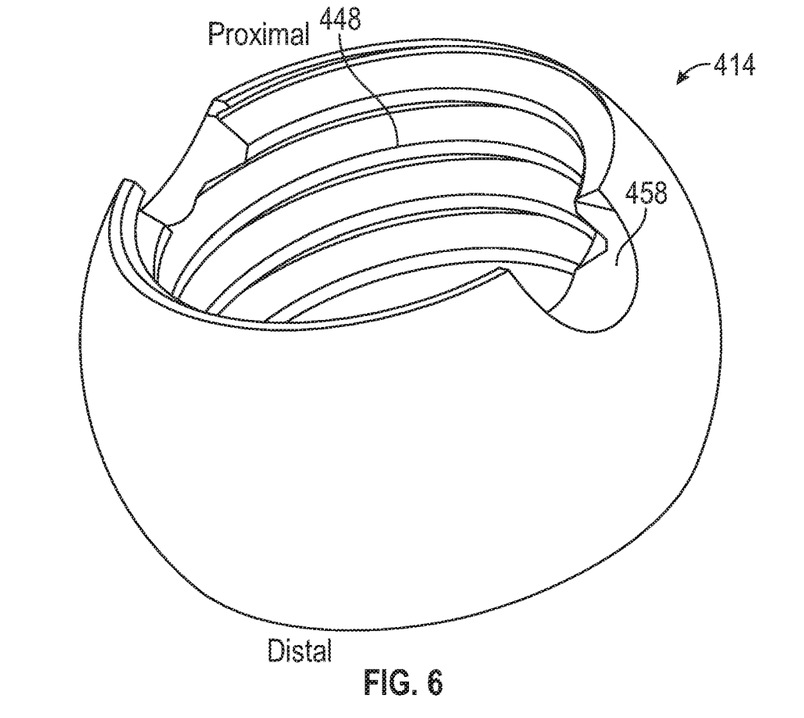
FIG. 6 illustrates an isometric view of a portion of an anchor assembly, in accordance with at least one example of this disclosure.
Figure 7:
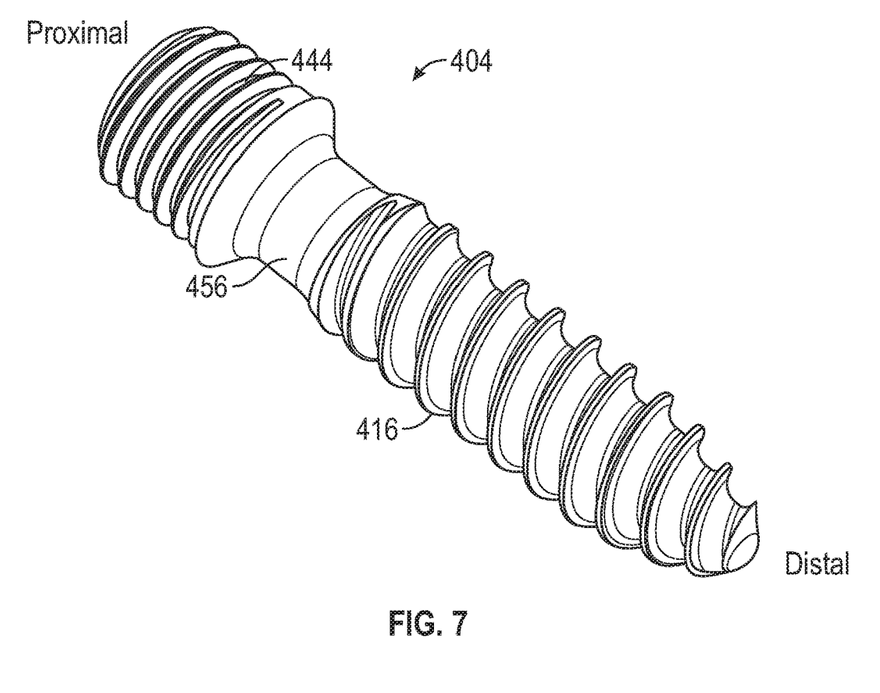
FIG. 7 illustrates an isometric view of a portion of an anchor assembly, in accordance with at least one example of this disclosure.

FIG. 6 illustrates an isometric view of the donut 414 of the anchor assembly 400, in accordance with at least one example of this disclosure. FIG. 7 illustrates an isometric view of the anchor 404 of the anchor assembly 400, in accordance with at least one example of this disclosure. Shown in FIGS. 6 and 7 are orientation indicators Proximal and Distal. FIGS. 6 and 7 are discussed below concurrently. The donut 414 and anchor 404 can be consistent with the descriptions above-further details of these components are shown and discussed below.

For example, FIG. 6 shows tool notches 458, which can be configured to receive a tool for applying a torque on donut 414 to secure the threaded portion 448 of the donut 414 to the proximal threaded portion 444 of the anchor 404. Also, FIG. 7 shows necked portion 456, which can have a relatively small diameter to help increase angulation of the shank 416 with respect to the housing 402.

In assembly of some examples, the donut 414 can be rotated 90 degrees and inserted into the central bore 418 of the housing 402 and then rotated 90 degrees to axially align with axis A of the housing 402. The threaded portion 444 of the anchor 404 can then be inserted distally-to-proximally into the housing 402 to engage the donut 414. A tool can then be used to engage the tool notches 458 of the donut and a torque can be applied to the donut to secure the proximal threaded portion 444 of the anchor 404 to the threaded portion 448 of the donut 414. In some examples, the proximal threaded portion 444 and the threaded portion 448 can have left-handed threading, or threading that is opposite of bone threaded of the shank 416.

Once the anchor 404 is secured to the donut 414, a tool can be inserted into notches 458 and a force can be applied thereto to deform threads of the threaded portion 448 radially inward to engage the threaded portion 444 of the anchor 404. Contact between the deformed portion of the notches 458 and the threaded portion 444 can help prevent backout or separation of the anchor 404 and the donut 414. In some examples, a distal perimeter seam of the donut 404 can be laser welded to the anchor 404. Then, the saddle 408 can be dropped over top of the donut 408.

Notes and Examples

The following, non-limiting examples, detail certain aspects of the present subject matter to solve the challenges and provide the benefits discussed herein, among others.

Example 1 is an anchor assembly couplable to bone, the assembly comprising: an anchor comprising: a shank securable to bone; and a head coupled to a proximal portion of the shank; a housing including an anchor bore extending distally into the housing along a longitudinal axis of the housing, the anchor bore configured to retain the head of the anchor therein; a turret couplable to a distal portion of the housing and configured to extend into the anchor bore, the anchor bore adapted to receive the head of the bone screw; and a lock receivable through an external side of the housing to secure the turret to the housing.

In Example 2, the subject matter of Example 1 optionally includes wherein the turret includes a proximal portion insertable into the housing and a distal portion extending therefrom, the proximal portion of the turret including a turret channel, wherein the lock is engageable with the turret channel to limit axial movement of the turret with respect to the housing when the lock is inserted into the housing.

In Example 3, the subject matter of Example 2 optionally includes wherein the housing further comprises a housing channel alignable with the turret channel when the turret is located within the anchor bore, the housing channel to receive the lock therein to, together with the turret channel, retain the lock therein to limit axial movement of the turret with respect to the housing.

In Example 4, the subject matter of Example 3 optionally includes wherein the housing further comprises a lock opening extending through the external side of the housing and connecting to the housing channel, the lock opening configured to receive the lock therethrough.

In Example 5, the subject matter of Example 4 optionally includes wherein the turret channel extends around an outer circumference of the proximal portion of the turret, and wherein the housing channel extends at least substantially around an inner circumference of the housing.

In Example 6, the subject matter of Example 5 optionally includes wherein the lock is a flexible spring bar or a cylindrical wire.

In Example 7, the subject matter of any one or more of Examples 5-6 optionally include wherein the lock is made of nitinol.

In Example 8, the subject matter of any one or more of Examples 1-7 optionally include a saddle receivable within the housing and configured to receive a connecting member thereon; wherein the turret further comprises a saddle bore configured to receive the saddle therein, the saddle configured to bias the turret outwards to limit the turret from compressing inward due to forces of the anchor and the connecting member.

Example 9 is an anchor assembly couplable to bone, the assembly comprising: an anchor comprising: a shank securable to bone; and a head coupled to a proximal portion of the shank; a housing including an anchor bore extending distally into the housing along a longitudinal axis of the housing, the anchor bore configured to retain the head of the anchor therein; and a turret couplable to a distal portion of the housing, the turret configured to retain the head of the anchor within the housing, the turret including a plurality of fingers configured to deflect radially inward to allow insertion of the proximal portion of the turret into the turret bore and biased to extend radially outward to engage the housing to secure the turret to the housing.

In Example 10, the subject matter of Example 9 optionally includes wherein the turret further comprises a proximal portion insertable into the distal portion of the housing and a distal portion extending distally from the proximal portion of the turret, the distal portion of the turret configured to engage the distal portion of the housing to limit proximal movement of the turret with respect to the housing, and the proximal portion including the plurality of fingers.

In Example 11, the subject matter of Example 10 optionally includes wherein the housing further comprises a turret bore configured to receive the proximal portion of the turret therein.

In Example 12, the subject matter of Example 11 optionally includes wherein the turret bore further comprises an undercut configured to receive the plurality of fingers to limit axial movement of the turret with respect to the housing.

In Example 13, the subject matter of Example 12 optionally includes wherein each finger of the plurality of fingers includes a barb extending radially outward and tapering inward as the barb extends distally, the barb configured to engage a proximal surface of the undercut to limit axially distal translation of the turret with respect to the housing.

In Example 14, the subject matter of any one or more of Examples 9-13 optionally include a saddle receivable within the housing and configured to engage the head of the anchor and configured to receive a connecting member thereon, the saddle including a saddle boss extending radially outward from an outer surface of the saddle; wherein the housing includes a boss slot configured to receive the saddle boss therein to limit rotation of the saddle with respect to the housing.

In Example 15, the subject matter of any one or more of Examples 9-14 optionally include a saddle receivable within the housing and configured to receive a connecting member thereon; wherein the plurality of fingers form a saddle bore on a radially inner surface of the plurality of fingers, the saddle bore configured to receive the saddle therein, the saddle configured to bias the plurality of fingers radially outwards to limit the plurality of fingers from deflecting radially inward due to forces of the anchor and the connecting member.

Example 16 is an anchor assembly couplable to bone, the assembly comprising: an anchor comprising: a shank securable to bone; and a proximal portion coupled to the shank; a housing including an anchor bore extending distally into the housing along a longitudinal axis of the housing, the anchor bore configured to retain the head of the anchor therein; and a head releasably couplable to the proximal portion of the anchor and disposable within a distal portion of the housing.

In Example 17, the subject matter of Example 16 optionally includes wherein the proximal portion of the anchor further comprises a first threaded portion and the head further comprises a second threaded portion threadably securable to the first threaded portion to retain the anchor within the housing.

In Example 18, the subject matter of any one or more of Examples 16-17 optionally include wherein the head further comprises a tool notch configured to receive a tool for applying a torque on the head to secure the first threaded portion to second threaded portion.

In Example 19, the subject matter of Example 18 optionally includes wherein the tool notch is configured to deform in response to a force from the tool to cause threads of the second threaded portion to deform radially inward to engage the first threaded portion to limit backout the anchor from the head.

In Example 20, the subject matter of any one or more of Examples 16-19 optionally include a saddle receivable within the housing and configured to engage the head and configured to receive a connecting member thereon.

In Example 21, the subject matter of Example 20 optionally includes wherein the saddle further comprises a ledge extending radially outward and tapered outward as the ledge extends distally to create a proximal-facing flat face, the ledge configured to engage the housing to limit axial movement of the saddle proximally with respect to the housing.

In Example 22, the subject matter of any one or more of Examples 20-21 optionally include wherein the saddle further comprises teeth extending proximally from the saddle, the teeth configured to engage a connecting member within the housing to limit movement of the connecting rod relative to the housing when the connecting member is compressed between a set screw and the saddle.

In Example 23, the subject matter of any one or more of Examples 20-22 optionally include wherein the saddle further comprises a ridge ridges to create teeth extending radially inward from an internal surface of the and toward a direction of the head of the anchor when the saddle is engaged with the head to help limit relative movement between the head and the saddle.

In Example 24, the system, device, or method of any one of or any combination of Examples 1-23 is optionally configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. An anchor assembly couplable to bone, the assembly comprising:
    an anchor comprising:
        a shank securable to bone; and
        a head coupled to a proximal portion of the shank;
    a housing including an anchor bore extending distally into the housing along a longitudinal axis of the housing, wherein the anchor bore is at least the diameter of the head of the anchor at the proximal end of the housing, the anchor bore configured to retain the head of the anchor therein, and the housing including a housing channel extending around an inner circumference of the housing;
    a turret couplable to a distal portion of the housing and configured to extend into the anchor bore;
    a lock receivable through an external side of the housing and into the housing channel to at least partially surround and engage the turret to secure the turret to the housing; and
    a saddle receivable within the housing and configured to receive a connecting member therein, wherein a proximal end of the turret further comprises a saddle bore configured to receive the saddle therein.

2. The assembly of claim 1, wherein the turret includes a proximal portion insertable into the housing and a distal portion extending therefrom, the proximal portion of the turret including a turret channel, wherein the lock is engageable with the turret channel to limit axial movement of the turret with respect to the housing when the lock is inserted into the housing.

3. The assembly of claim 2, wherein the housing channel is alignable with the turret channel when the turret is located within the anchor bore, the housing channel to receive the lock therein to, together with the turret channel, retain the lock therein to limit axial movement of the turret with respect to the housing.

4. The assembly of claim 3, wherein the housing further comprises a lock opening extending through the external side of the housing and connecting to the housing channel, the lock opening configured to receive the lock therethrough.

5. The assembly of claim 4, wherein the turret channel extends around an outer circumference of the proximal portion of the turret, and wherein the housing channel extends at least substantially around an inner circumference of the housing.

6. The assembly of claim 5, wherein the lock is a flexible spring bar or a cylindrical wire.

7. The assembly of claim 5, wherein the lock is made of nitinol.

8. The assembly of claim 1, the saddle configured to bias the turret outwards to limit the turret from compressing inward due to forces of the anchor and the connecting member.

9. The assembly of claim 1, wherein the turret is couplable to the distal portion of the housing prior to an insertion of the anchor into a proximal portion of the housing, and wherein the saddle is receivable within the proximal portion of the housing after the insertion of the anchor into the proximal portion of the housing.

10. The assembly of claim 1, wherein the anchor bore is at least the diameter of the head of the anchor for the length of the housing.

11. An anchor assembly couplable to bone, the assembly comprising: an anchor comprising:
    a shank securable to bone; and
    a head coupled to a proximal portion of the shank;
    a housing defining:
    an anchor bore extending distally into the housing along a longitudinal axis of the housing, wherein the anchor bore is at least the diameter of the head of the anchor at the proximal end of the housing, the anchor bore configured to retain the head of the anchor therein;
    a housing channel extending around an inner circumference of the housing; and
    a lock opening extending through an external side of the housing and connected to the housing channel;
    a turret couplable to a distal portion of the housing and configured to extend into the anchor bore;
    a lock receivable through the lock opening and into the housing channel to engage the turret and the housing to secure the turret to the housing; and
    a saddle receivable within the housing and configured to receive a connecting member therein;
    wherein a proximal end of the turret further comprises a saddle bore configured to receive the saddle therein, the saddle configured to bias the turret outwards to limit the turret from compressing inward due to forces of the anchor and the connecting member.

12. The assembly of claim 11, wherein the turret includes a proximal portion insertable into the housing and a distal portion extending therefrom, the proximal portion of the turret including a turret channel, wherein the lock is engageable with the turret channel to limit axial movement of the turret with respect to the housing when the lock is inserted into the housing, the turret channel alignable with the housing channel when the turret is located within the anchor bore, the turret channel to receive the lock therein to, together with the housing channel, retain the lock therein to limit axial movement of the turret with respect to the housing.

13. The assembly of claim 12, wherein the turret channel extends around an outer circumference of the proximal portion of the turret, and wherein the housing channel extends at least substantially around an inner circumference of the housing.

14. The assembly of claim 13, wherein the lock is a flexible spring bar or a cylindrical wire.

15. The assembly of claim 14, wherein the lock is made of nitinol.

16. The assembly of claim 11, wherein the turret is couplable to the distal portion of the housing prior to an insertion of the anchor into a proximal portion of the housing, and wherein the saddle is receivable within the proximal portion of the housing after the insertion of the anchor into the proximal portion of the housing.

17. The assembly of claim 11, wherein the anchor bore is at least the diameter of the head of the anchor for the length of the housing.

18. An anchor assembly couplable to bone, the assembly comprising:
- an anchor comprising:
  - a shank securable to bone; and
  - a head coupled to a proximal portion of the shank;
- a housing including an anchor bore extending distally into the housing along a longitudinal axis of the housing, wherein the anchor bore is at least the diameter of the head of the anchor at the proximal end of the housing, the anchor bore configured to retain the head of the anchor therein;
- a turret couplable to a distal portion of the housing and configured to extend into the anchor bore; and
- a saddle receivable within the housing and configured to receive a connecting member therein, wherein a proximal end of the turret further comprises a saddle bore configured to receive the saddle therein.

* * * * *